United States Patent [19]

Simons et al.

[11] Patent Number: 5,562,211
[45] Date of Patent: Oct. 8, 1996

[54] STERILE PACKAGE HAVING DOUBLE-SIDED TAPE FOR MOUNTING

[75] Inventors: Traci M. Simons, Piscataway, N.J.; Robert J. Cerwin, Pipersville, Pa.; Michael D. O'Toole, Suffern, N.Y.

[73] Assignee: Ethicon, Inc., Somerville, N.J.

[21] Appl. No.: 287,440

[22] Filed: Aug. 8, 1994

[51] Int. Cl.⁶ .................................................. B65D 83/00
[52] U.S. Cl. ........................... 206/438; 206/484; 206/813
[58] Field of Search .................................. 206/440, 441, 206/63.3, 484, 438, 813

[56] References Cited

U.S. PATENT DOCUMENTS

| | | | |
|---|---|---|---|
| 2,633,440 | 3/1953 | Scholl | 154/53.5 |
| 3,835,992 | 9/1974 | Adams, IV | 206/441 X |
| 3,861,521 | 1/1975 | Burtz | 206/63.3 |
| 4,097,627 | 6/1978 | Nemeth et al. | 428/40 |
| 4,546,022 | 10/1985 | Madonia et al. | 428/31 |
| 4,787,380 | 11/1988 | Scott | 206/441 X |
| 4,857,066 | 8/1989 | Allison | 604/385.1 |
| 5,040,903 | 8/1991 | Schramer | 206/813 X |
| 5,301,807 | 4/1994 | Donahue | 206/370 |

*Primary Examiner*—Jacob K. Ackun
*Attorney, Agent, or Firm*—Emil Richard Skula

[57] ABSTRACT

A sterile package for medical devices. A double sided tape is mounted to the bottom outer side of the package. The package is contained within a sealed outer package. The double sided tape has a release liner which has a periphery larger than the periphery of the adhesive coating on the double sided tape.

4 Claims, 4 Drawing Sheets

STERILE PACKAGE HAVING DOUBLE-SIDED TAPE FOR MOUNTING

TECHNICAL FIELD

The field of art to which this invention pertains is packaging, in particular, sterile packages for medical devices.

BACKGROUND OF THE INVENTION

In order to minimize the threat of infection to a patient during a surgical procedure, it is necessary that only sterile medical devices be used. Furthermore, strict adherence to sterile procedures is required to prevent the devices from becoming contaminated prior to use, especially during and after removal of the medical devices from sterile packages. In order to remove a sterile medical device from a sterile package, it is typically necessary for the medical professional to grasp the package with one hand while grasping and removing the device with the other hand. One type of sterile medical device which is frequently used is a surgical needle and suture combination. It is typical for most manufacturers to mount one or more needle and suture combinations in a primary suture package. Various surgical procedures require that multiple sutures be mounted in single primary package. As mentioned previously, surgical needles and sutures are mounted in a primary package which is then inserted into an outer package. The outer package is sealed and the entire combination is sterilized using conventional sterilization processes resulting in the needles, sutures, primary package and interior of the outer package being sterile. During a typical surgical procedure a circulating nurse opens the outer package while a scrub nurse removes the sterile inner primary package to complete the sterile transfer or a circulating nurse removes the sterile inner, primary package by opening the outer package and flipping it from the outer package onto a sterile tray in a sterile field without touching the sterile primary package.

During most surgical procedures, the surgeon requires the use of both hands when suturing. For example, one hand will be used to hold a needle grasper while the other hand will be used to manipulate tissue, organs, the incision, blood vessels, etc. Needles are grasped and removed from a primary surgical needle and suture package using the needle grasper. A needle grasper typically has plier-like jaws for holding a needle. The surgeon manipulates the needle grasper to push and pull the needle through tissue.

In order to eliminate the need for a surgeon or an assistant to hold a primary needle package while withdrawing needles and sutures, manufacturers have mounted strips of conventional double-sided tape to the exterior of primary needle and suture packages. The top side of the tape is typically mounted to the bottom exterior surface of the package. By pealing off a conventional release liner mounted to the bottom side of the tape to expose a bottom adhesive coating, the primary suture package may then be mounted to a surgical drape or other surface by pressing the package and exposed bottom adhesive coating against the surgical drape or surface. The surgeon may then pull needles and sutures from the primary package with one hand while having the other hand free.

Although the use of double sided tape has proven to be effective in mounting medical device packages such as primary surgical needle and suture packages to drapes and other surfaces, there are also disadvantages attendant with its use. Specifically, it is known that most conventional adhesives used to coat the surfaces of double-sided tape tend to flow when exposed to the environment of a typical sterilization process. This can cause the adhesive to migrate off of the tape surface beyond the periphery of a release liner and onto the outer surface of the primary package in which the sterile medical device is housed.

If the adhesive flows in such a manner beyond the periphery of a release liner and contacts the interior of the outer package, it may be difficult for a scrub nurse, circulating nurse, or other medical professional to remove the primary package from the outer package in the sterile field without compromising the sterility of the package. The adhesive may cause the primary package to stick to the outer package. Consequently, the circulating nurse would not be able to flip the package into the sterile field. If the primary package released at an inappropriate time during flipping because of sticking, the primary package could be misdirected out of the sterile field. Another concern would be if the primary package released and slid over the edge of the outer package and then landed in the sterile field. This situation would result in the contamination of the sterile field. The edge of the outer package is nonsterile. In addition, it may be necessary to grasp the outer surface of the outer package in order to remove the primary package, and, the outer surface of the outer package is not sterile. Therefore, grasping the primary package after having grasped the exterior of the outer package could result in the compromise of the sterility of the primary package and its contents.

Accordingly, there is a need in this art for improved sterile medical device packages having double-sided tape mounted to their exteriors for use in mounting the packages to surgical drapes or various other surfaces in the operating room.

DISCLOSURE OF THE INVENTION

Therefore, it is an object of the present invention to provide a sterile package having a double-sided tape laminate mounted thereto which prevents adhesive on the surface of the tape from contacting the interior of an outer package during shipping, handling, sterilization and storage.

Accordingly, a sterile package is disclosed. The sterile package has an outer package having an interior and an exterior. The outer package contains a sterile inner, primary package. The primary package has an inner surface and an outer surface and a tape laminate mounted to the exterior surface. The tape laminate has a substantially flat tape member. The flat tape member has a top surface, a bottom surface, and an outer periphery. The top surface has a top coating of adhesive, and the bottom surface also has a bottom coating of adhesive. A release liner member having an outer periphery is mounted to said bottom adhesive coating. The outer periphery of the release liner member is sufficiently larger than the outer periphery of the flat tape member to prevent adhesive from flowing beyond the outer periphery of the release liner member, and thereby prevent the adhesive coating from contacting the interior of the outer package. The top surface of the flat member is mounted to the outer surface of the primary package by contacting the top adhesive coating with the outer surface of the primary package. The primary package and tape laminate are contained in an outer package which is sealed prior to sterilization.

Another aspect of the present invention is a laminate used with a sterile package for affixing the sterile package to a surface. The laminate has a bottom release liner. The bottom release liner has an elongated strip configuration and as such may be spooled to create a continuous roll for automated application. A plurality of flat tape members each having an outer periphery, a top surface and a bottom surface, and each having a bottom adhesive coating and a top adhesive coating are mounted to the bottom release liner, spaced apart equidistantly, such that the bottom adhesive coating of each tape member is in contact with the bottom release liner. A top release liner having an outer periphery is mounted to the top of each flat tape member such that the top adhesive coating is in contact with the top release liner. The outer periphery of each flat tape member is substantially equivalent to the outer periphery of each top release liner. The bottom release liners are mounted to the bottom adhesive coating of each tape member such that the outer peripheries of the tape members and the bottom release liners are substantially coextensive.

Yet another aspect of the present invention is a laminate used with a sterile package for affixing the sterile package to a surface. The laminate has a bottom release liner having an outer periphery. A flat tape member having an outer periphery, a top surface and a bottom surface and having a bottom adhesive coating and a top adhesive coating is mounted to the bottom release liner such that the bottom adhesive coating of the tape member is in contact with the bottom release liner. A top release liner having an outer periphery is mounted to the top of the flat tape member such that the top adhesive coating is in contact with the top release liner. The outer periphery of the flat tape member is substantially equivalent to the outer periphery of the top release liner. The top release liner is mounted to the top adhesive coating of the tape member such that the peripheries of the tape member and the top release liner are substantially coextensive. The bottom release liner is mounted such that the bottom release liner is centered upon the tape member and the outer periphery of the release liner extends beyond the outer periphery of the tape member.

DESCRIPTION OF PREFERRED EMBODIMENT

Figure 1:
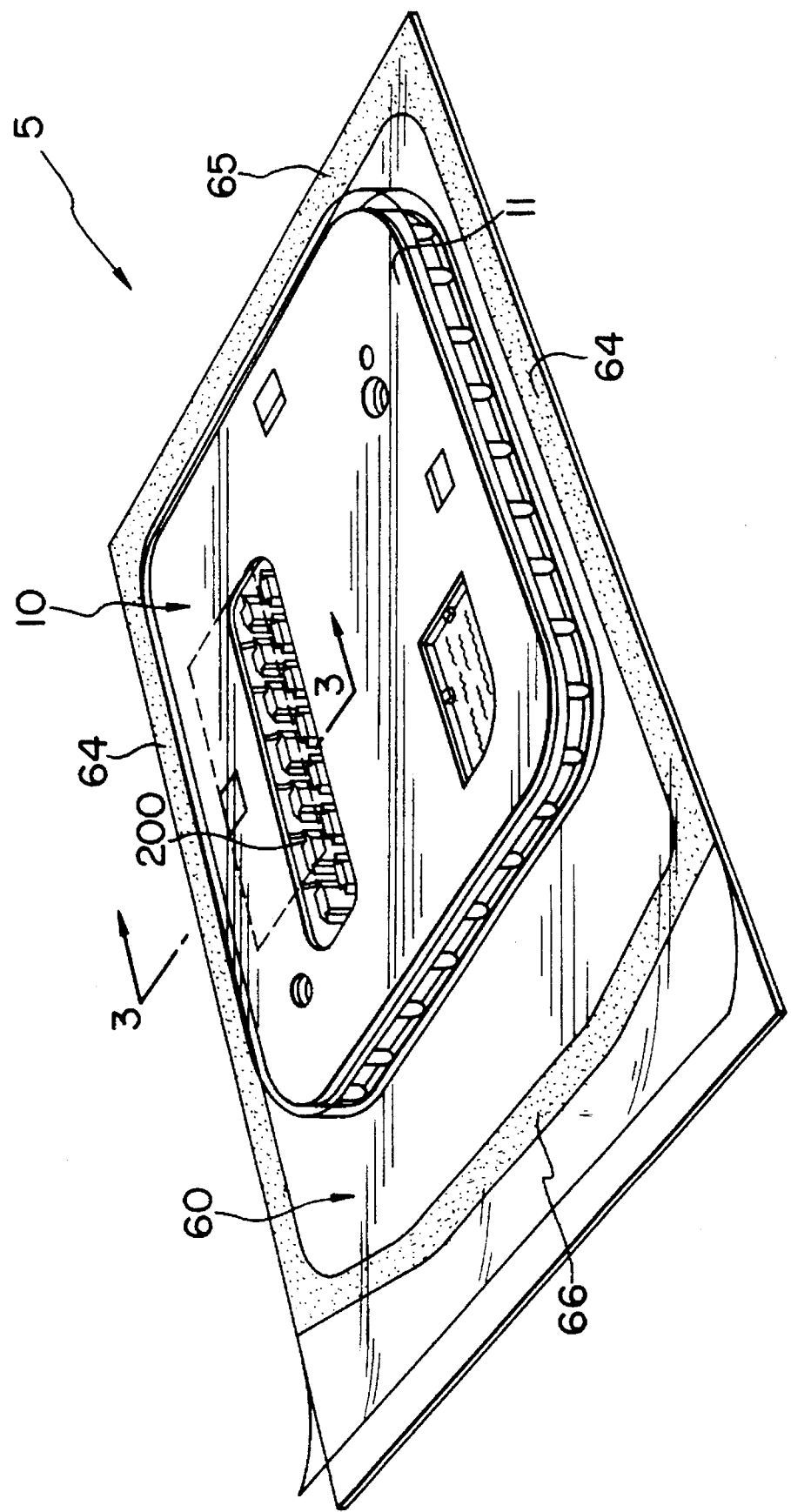
FIG. 1 is a perspective view of a sterile package of the present invention having a strip of double-sided tape laminate mounted to the bottom of a primary inner surgical needle and suture package which is contained within an outer envelope.
Figure 2:
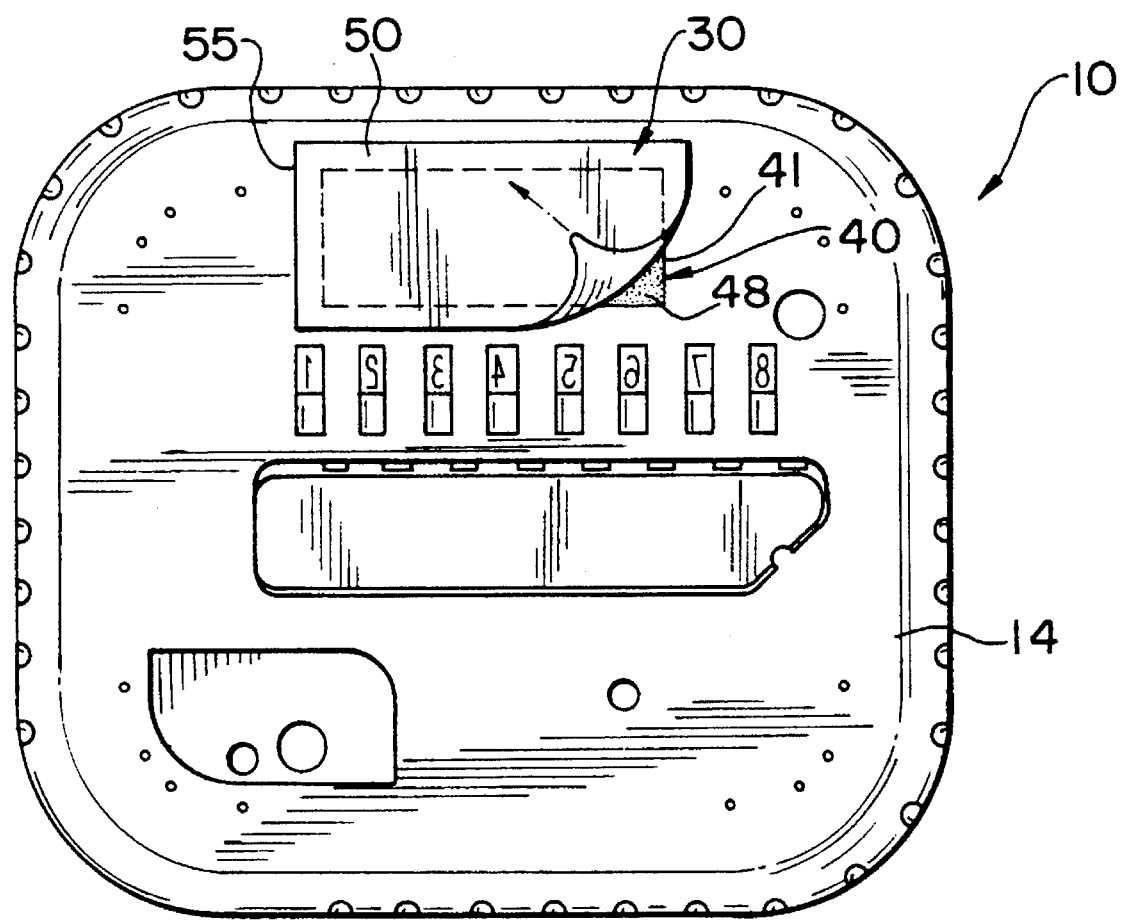
FIG. 2 is a bottom view of the package of FIG. 1 illustrating a double-sided tape laminate of the present invention mounted to the bottom of the primary package; the bottom release liner is illustrated partially pealed away from the bottom of the tape member and is seen to overhang the tape member.
Figure 3:
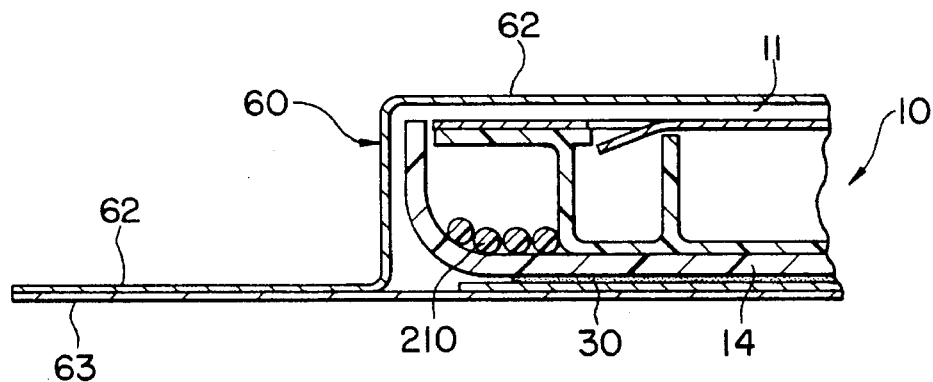
FIG. 3 is a cross-sectional view of the package of FIG. 1 taken along View Line 3—3.
Figure 4:
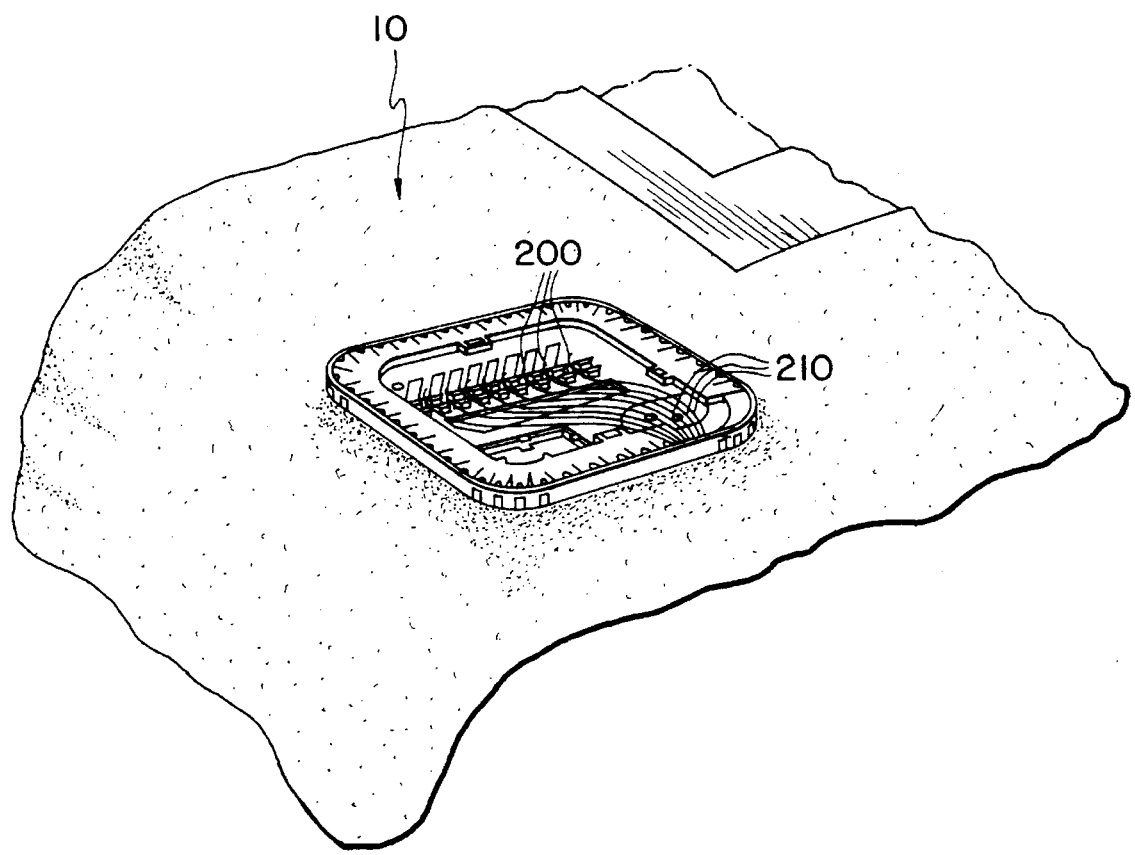
FIG. 4 is a perspective view illustrating the inner, primary package of the package of FIG. 1 mounted to a surgical drape during a surgical procedure.

A sterile package 5 of the present invention is illustrated in FIG. 1. The package 5 is seen to consist of a sterile inner, primary medical device package 10 and an outer sealed package 60. Package 10 is a primary package for housing a plurality of surgical needles 200 and sutures 210, although package 10 may also have other medical device package configurations and equivalents thereof. Referring also to FIGS. 2 and 3, the package 10 is seen to have a top surface 11 and a bottom outer surface 14. Sutures 210 and surgical needles 200 are seen to be mounted in the package 10. A package similar to package 10 is further described in U.S. Pat. No. 5,230,424 which is incorporated by reference. It will be appreciated by those skilled in the art that any type of conventional suture package may be used in the practice of the present invention as well as any type of conventional medical device package.

Referring also to FIGS. 2, 3, 4 and 5, a double-sided tape laminate tape strip 30 is seen to be mounted to the bottom outer surface 14 of package 10. The tape laminate 30 is seen to consist of a substantially flat member 40 having an outer periphery 41 (see FIG. 6). Flat member 40 is preferably rectangularly shaped having a pair of opposed major sides and a pair of opposed minor sides, but may have any shape including square, polygonal, circular, elliptical and the like. Flat member 40 is seen to have top surface 42 and bottom surface 46. Flat member 40 is also seen to have top adhesive coating 44 on top surface 42 and bottom adhesive coating 48 covering bottom surface 46. It is preferred that the adhesive coating cover the entire top and bottom surface areas, however, the coatings may be applied to certain sections of the surfaces if so desired.

Bottom release liner 50 is seen to be mounted to coating 48. Bottom release liner 50 is seen to have an outer periphery 55. Release liner 50 is seen to be rectangularly shaped having a pair of opposed major sides and a pair of opposed minor sides, but may have any configuration. Bottom release liner 50 has outer periphery 55 which is sufficiently larger than the periphery 41 of flat member 40 to effectively prevent top and bottom adhesive coatings 44 and 48 from coming into contact with an outer package during or after or sterilization, and during shipping and handling and storage of package 10 should the coatings 44 and 48 flow off from surfaces 42 and 46. Typically, the outer periphery 55 of release liner 50 will typically overlap the periphery 41 of tape member 40 by about 0.125" to about 0.5", preferably about 0.25". If desired, a side or corner of the bottom release liner 50 may be bent or folded to facilitate grasping by a gloved hand, provided that the flat member 40 remains sufficiently covered to effectively prevent the adhesive coatings from flowing beyond periphery 55.

The outer package 60 is seen to have upper and lower flat members 62 and 63. Flat members 62 and 63 are joined by side seams 64, bottom seam 65 and top seam 66. Package 60 is seen to be a conventional outer envelope-type or pouch-type package for housing sterile medical devices. It will be appreciated that side seams 64 could be eliminated if flat members 62 and 63 are replaced with a tubular member.

Flat member 40 will typically be manufactured from conventional materials and equivalents thereof including polymeric films including polyethylene, polyester, ethylene vinyl acetate, polyvinylchloride; foam products including polyurethane, polyethylene, and polyvinylchloride; and, woven or nonwoven materials including rayon and polyethylene.

Adhesive coatings 44 and 48 will consist of conventional adhesives and equivalents thereof having sufficient adhesive properties to effectively attach the organizer package to a typical surface encountered in an operating room, such as a surgical drape, while allowing dispensing of the needles contained therein. Examples of adhesives useful in the practice of the present invention include National Starch Durotac® #80-1065 available from National Starch located in Bridgewater, N.J., 3M #1509 and #1522 available from 3M Co. located in Minneapolis-St. Paul, Minn.

Release liner 50 may be manufactured from #80 silicone-treated bleached Kraft-glassine paper and the like. Liner 50 will have a conventional coating with release properties that are sufficient to effectively release from adhesive coating 48 when the liner 50 is pulled. Coatings which may be used include silicone, polyethylene, and the like.

Tape laminate 30 may be manufactured in the following manner. A continuous strip of double-sided tape is manufactured in a conventional manner. A laminate 150 having both an bottom release liner 50 and an outer release liner 70 is produced. This is in contrast to conventional double-sided tapes which typically utilize only a single release liner. Only a single liner is needed with such conventional tapes since as coils of tape are wound onto a roll, the outer positioned release liner of a wound tape coil serves as a release liner for the inner adhesive side of coils of subsequently wound tape.

Figure 5:
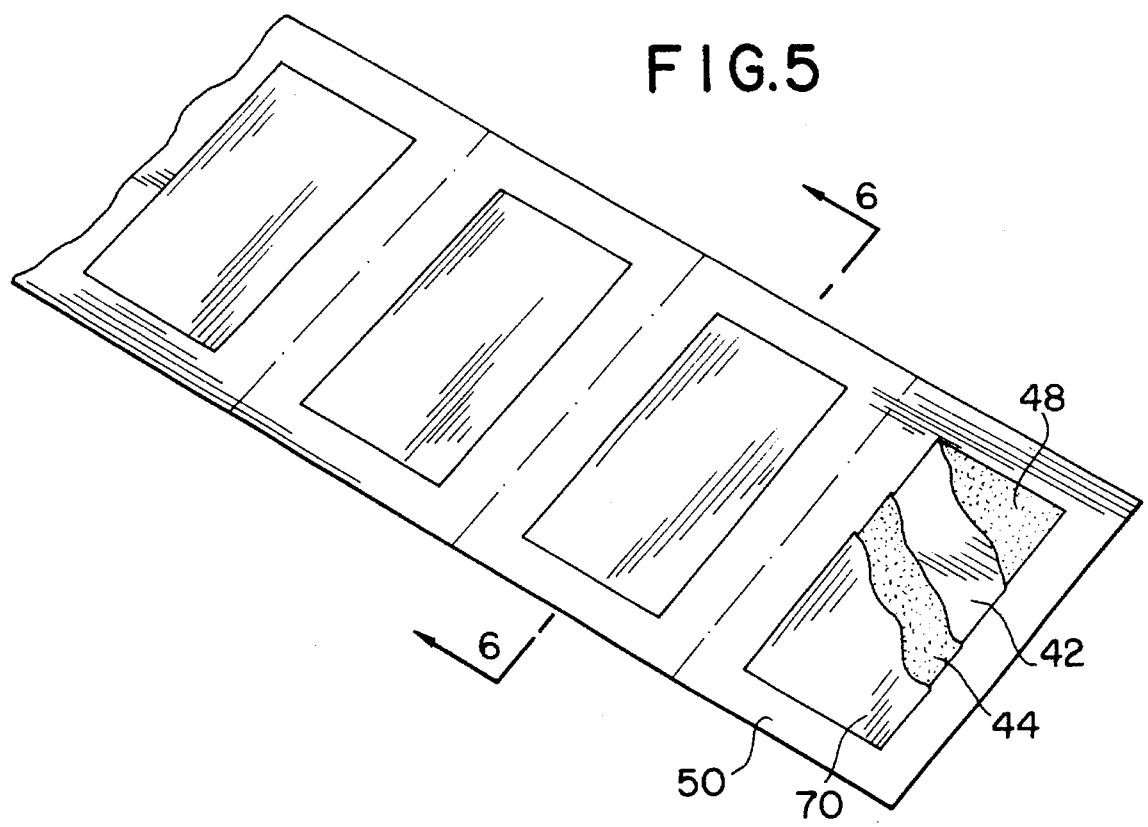
FIG. 5 is a perspective view a double-side tape laminate of the present invention prior to cutting the bottom release liner.
Figure 6:
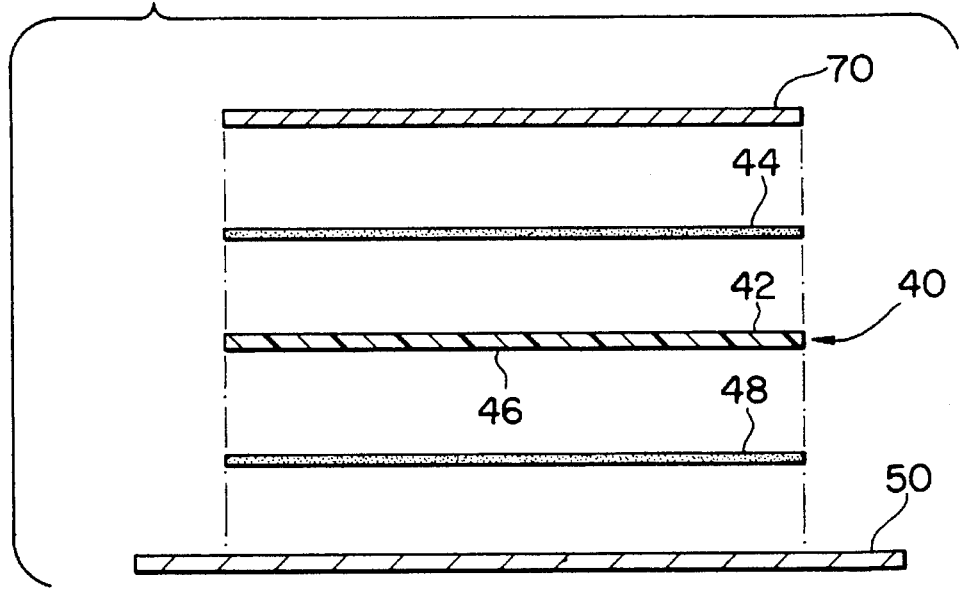
FIG. 6 is a cross-sectional view of a double-sided tape laminate of the present invention illustrating the larger outer periphery of the bottom release liner.

The laminate 150 is then subjected to a die-cutting operation in which die-cuts are made through the top release liner 70 and tape member 40 leaving the bottom release liner 50 intact. The die cut portions of release liner 70 and tape 40 are then stripped leaving a continuous bottom release liner 50 with a series of double-coated tape members 40 having outer release liners 70 of equal size as seen in FIG. 5. The outer peripheries of top release liner 70 and tape member 40 are coextensive. The members 40 are preferably equidistantly spaced on liner 50. In order to form tape laminates 30, the release liner 50 is cut between adjacent tape members 40 forming laminates 30 each having a top release liner 70, a tape member 40 having top and bottom adhesive coatings 44 and 48, and bottom release liner 50 having an outer periphery 55 greater than the outer periphery 41 of tape member 40. The laminate 30 may then be applied to a medical device package by removing top release liner 70. This application may be accomplished in a fully-manual, semi-automatic, or fully-automatic manner by removing top release liner 70 and affixing tape member 40 to the exterior of the medical device package by contacting the top adhesive coating 44 with the exterior of the medical device package.

The outer package 60 may be made from conventional materials including foils, laminate films, papers, Tyvek®, and the like. The outer package 60 is sealed in a conventional manner, e.g., heat sealing, adhesives, ultrasonics, welding, and the like.

The primary package 10 is placed in an outer package 60 and sealed in a conventional manner to form package 5. The package 5 is sterilized using conventional sterilization techniques including cobalt irradiation, electron beam exposure, ethylene oxide gas, steam and/or heat sterilization, gas plasma sterilization, chemical sterilants, and the like.

The package 5 is opened in accordance with conventional sterile procedures by a medical professional, such as a circulating nurse, in the following manner. The circulating nurse opens the outer package 60 while the scrub removes the inner, sterile primary package 10 or the circulating nurse opens the package 60 and flips the package 10 into the sterile field.

The primary package 10 is mounted to a surgical drape or other surface by a medical professional in the following manner. The release liner 50 is removed and the package 10 is pressed against the surgical drape or surface with sufficient pressure to ensure effective adhesion and mounting.

The packages 5 of the present invention utilizing tape laminate 30 have the advantages of using double-sided tape to mount primary packages to surgical drapes or surfaces, however the flow of adhesive coatings from the tape member 40 to the inner surface of the outer package is substantially eliminated, thereby decreasing the likelihood of compromising the sterility of the primary package and its contents. Adjunctly, the larger periphery 55 of release liner 50 enables easier grasping and removal of release liner 50 by the gloved hand of the scrub nurse.

Although this invention has been shown and described with respect to detailed embodiments thereof, it will be understood by those skilled in the art that various changes in form and detail thereof may be made without departing from the spirit and scope of the claimed invention.

We claim:

1. A sterile package, comprising:
   a) an inner sterile primary package for receiving a medical device having a top outer surface and a bottom outer surface;
   b) a laminate comprising:
      a substantially flat tape member having a top surface and a bottom surface and an outer periphery;
      a top coating of adhesive on said top surface and a bottom coating of adhesive on said bottom surface; and,
      a bottom release liner member mounted to said bottom adhesive coating, the release liner having an outer periphery such that the outer periphery of the release liner is sufficiently larger than the outer periphery of the flat tape member to effectively prevent the bottom coating of adhesive from flowing beyond the outer periphery of the release liner after sterilization of the inner sterile primary package, wherein the top adhesive coating of the flat tape member is mounted to the bottom outer surface of the primary package; and,
   c) a sealed outer package in which the sterile primary package is contained.

2. The package of claim 1 wherein the outer package comprises a metal foil.

3. The package of claim 1 wherein the outer package comprises polymeric film.

4. The package of claim 1 wherein a section of the periphery of the bottom release liner is sufficiently folded to facilitate effective grasping by a gloved hand.

* * * * *